United States Patent [19]

Jordan

[11] 4,018,876

[45] Apr. 19, 1977

[54] PROCESS FOR THE PRODUCTION OF METAL OXALATES AND SODA ASH

[76] Inventor: Robert Kenneth Jordan, The Carlton House, Suite 1431, 550 Grant St., Pittsburgh, Pa. 15219

[22] Filed: Mar. 4, 1975

[21] Appl. No.: 555,189

[52] U.S. Cl. .............................. 423/421; 260/538
[51] Int. Cl.² .................. C07C 55/06; C01B 31/24
[58] Field of Search ........... 260/538, 527 R, 526 R; 423/419–422, 430

[56] References Cited

UNITED STATES PATENTS 1,687,480  10/1928  Buchanan et al. .................. 260/538
2,002,342  5/1935   Enderli .............................. 260/538

OTHER PUBLICATIONS

Alien Property Custodian (APC) 227107, Suzuki, H., filed Aug. 27, 1938, published Apr. 20, 1943.

*Primary Examiner*—O. R. Vertiz
*Assistant Examiner*—Gary P. Straub

[57] ABSTRACT

A process for the simultaneous production of relatively insoluble metal oxalates and carbonates and bicarbonates of alkali metals and ammonium in which a metal carbonate and an ammonium or alkali metal oxalate are combined in water or methanol, optionally with the addition of carbon dioxide.

3 Claims, No Drawings

PROCESS FOR THE PRODUCTION OF METAL OXALATES AND SODA ASH

This invention relates to a process for the simultaneous production of metal oxalates and ammonium or alkali metal carbonates from metal carbonates and ammonium or alkali metal oxalates.

The carbonates of many metals exist in great abundance in nature, examples include soda ash, limestone, dolomite, siderite, rodochrosite, smithsonite, azurite, spherocobaltite, cerussite, zaratite and magnesite to name a few. Soda ash is usually found in the mineral trona, but large deposites are located far from the marketplace. And although much trona is chemically processed to produce both soda ash and bicarbonate of soda, high rail transportation costs in the United States have made these chemicals relatively expensive for the glass and detergent industries that are respectively their major consumers.

The major uses for limestone in the chemical industry generally require that it first be calcined to lime. For example in the Solvay soda ash process, ammoniated brine is carbonated to precipitate out bicarbonate of soda, leaving a solution comprised essentially of ammonium chloride and which necessarily must be treated with hydrated lime to recover the expensive ammonia. In the past when all forms of energy were cheap, the cost of lime was a minor factor in the overall cost of Solvay soda ash, but this is no longer true. Another factor in the Solvay process is the disposal of huge quantities of calcium chloride solution which has resulted in closing a number of soda ash facilities.

Soda ash and bicarbonate of soda can be made by the carbonation of caustic soda, which is how practically all potassium carbonate and bicarbonate is made. But potassium hydroxide and sodium hydroxide are produced by the electrolysis of the corresponding chloride, an energy intensive and not inexpensive process. While the processing of trona has supplanted the closed down synthetic soda ash production, the cost to the glass industry has risen mostly because of rail transportation. Potassium carbonate has a number of uses, the fastest growing use appears to be in the removal of carbon dioxide and sulfur containing compounds from natural gas and chemical process gas streams.

Limestone and dolomite are plentiful in most parts of the United States and the world, but again chemical utility necessitates that they be calcined, a process requiring an average of more than 5 million btus per ton of lime or dolime. As dolomite and magnesite are excellent sources of magnesium ion, for examples for magnesia and magnesium metal, low cost ways to produce magnesium compound intermediates which avoid calcination are needed. Manganese carbonate, rodochrosite, is available throughout much of the world, but is not the preferred manganese ore in spite of the fact that in the form of the carbonate, manganese has a valence of 2 compared to 3 and 4 for the oxide ores. The problem is that the carbonate ion is bulky and represents no value when shipped, only a cost. But again, calcination to remove the carbon dioxide is expensive so that in spite of its wide availability, manganese carbonate is not widely used as a starting material for manganese dioxide, manganese metal or ferromanganese. Again a process is needed to directly convert manganese carbonate into useful intermediates.

Even considerable ferrous carbonate is available, but as iron ore, $Fe_2O_3$ is very cheap, there is no interest in it. But other valuable carbonate ores or metal carbonate intermediates could be available if there were and inexpensive direct way to process them to useful intermediates. As noted above, nickel, copper, zinc and other metals are found in nature as natural carbonates, or in their processing could be economically extracted as their carbonates.

In a number of copending applications I disclose a series of processes which among other things promises to make oxalates, especially sodium oxalate, most economically, essentially from common salt and carbon monoxide. As carbon monoxide is potentially available in great quantities at low cost from blast furnaces and as salt is already very cheap, low cost oxalates could provide the basis for a new kind of chemical venture. As sodium oxalate is made now, caustic soda is carbonylated with carbon monoxide to yield a solution of sodium formate which is evaporated to dryness, carefully melted at about 263° C and then rapidly heated to about 400° C for 5 to 10 minutes causing fusion to sodium oxalate with the evolution of hydrogen. The sodium oxalate is quenched by dumping it in water. Treatment of the solution or slurry with hydrated lime causes the precipitation of calcium oxalate and yields a solution of sodium hydroxide which is some-concentrated before recycling in the process. Calcium oxalate is treated with a large excess of dilute sulfuric acid at about 70° C to first precipitate calcium sulfate, and then on cooling the dihydrate of oxalic acid crystallizes out. Again the liquor is recycled. Clearly, as sodium oxalate by my processes can be made from salt and carbon monoxide, the causticization of sodium oxalate to yield caustic soda is tantamount to a method for the nonelectrolytic production of caustic soda. Also, it is obvious that by carbonation the caustic soda, sodium carbonate and sodium bicarbonate can be made. But again, the causticizing with lime is expensive if it is desired to make sodium carbonates. Heretofore however, these steps were well known and would have been necessary in the production of sodium or potassium carbonates via oxalate chemistry.

Metal oxalates have a wide range of very useful properties. Nickel, copper and a number of other metal oxides decompose to the metals at only 300°–400° C. Likewise, iron and cobalt oxalates in an atmosphere of hydrogen decompose to the metals at only slightly higher temperatures, like 450° C and other metal oxalates behave similarly. For example, manganous oxalate decomposes in hydrogen or nitrogen to yield mainly the lower oxide, but as the product is very oxygen sensitive, some manganese metal may be present. Mixtures of metal oxalates are often easily separated, for example magnesium and calcium oxalates can be treated with caustic soda in which magnesium oxalate is relatively soluble. Manganese carbonate as found naturally is usually contaminated with iron oxide, $Fe_2O_3$, but manganous oxalate is essentially insoluble while ferric oxalate is very soluble. Fortuitously a great amount of oxalate chemistry is well known, so that if new processes for their production are developed, practical uses are instantly available. Therefore, it is an object of my invention to provide a new and improved process for the production of sodium and potassium carbonates and bicarbonates.

It is another object to provide a new and improved process for the production of insoluble metal oxalates.

It is a further object to provide a new and improved process for the production of calcium oxalate.

My invention is a process for the production of insoluble metal oxalates and alkali metal and ammonium carbonates wherein a metal carbonate and an alkali metal or ammonium oxalate are combined in water or methanol, or mixtures thereof, optionally with the addition of carbon dioxide at a temperature in the range of from about −30° to about 300° C.

I have unexpectedly discovered that the addition of finely divided limestone to a solution of sodium oxalate causes an immediate and rapid rise in pH to about 11, where the process appears to cease. Thus when equimolar quantities of limestone and sodium oxalate are mixed in water at about 50° a conversion of somewhat over 40 percent is realized and a measurable increase in temperature is noted. As the pH approaches 11, the process comes to a halt, but if carbon dioxide is bubbled in, presumably lowering the pH by converting the sodium carbonate to sodium bicarbonate, the conversion can be increased to almost completion. Clearly this offers a remarkable route to soda ash and bicarbonate of soda if sodium oxalate can be produced cheaply, obviating the necessity to make lime. As potassium oxalate is also easily made by fusion of its formate, it was tried under similar conditions and found to behave likewise. While lithium oxalate is not readily made like sodium oxalate, it was also used with like results with calcium carbonate. Ammonium oxalate also works.

A series of experiments were then conducted to determine the versatility of the process with a large number of metal carbonates. It was found that the carbonate of any metal having an insoluble oxalate operates in the process. Magnesium carbonate behaves almost exactly like limestone and the same can be said for dolomite. The conversions obtained initially with other carbonates vary, but on addition of carbon dioxide the process can be made to go to essential completion. Thus $Cu_2CO_3$, malachite, rodochrosite, thorium carbonate, nickel carbonate, siderite, spherocobaltite, $Ag_2CO_3$, cerussite, witherite and smithsonite tested successfully. The only criteria is that the resulting oxalate be relatively insoluble, even though the alkali metal and ammonium complexes may have considerable solubility.

The process is essentially independent of the relative concentrations within reasonable limits, but particle size greatly affects the rate. While in time small chunks of calcite can be digested in an excess of sodium oxalate, rapid rates are obtained using powdered carbonates, i.e., less than 200 mesh though reasonable rates can had with 100 mesh calcite.

The process can be operated over a wide range of temperatures, especially when using finely divided metal carbonates. But there is a problem at lower temperatures when it is desired to obtain high conversions in that the alkali carbonate concentration causes the pH to rise rapidly, thus in effect stopping the process. On adding carbon dioxide the pH drops, but as the alkali metal bicarbonate is relatively insoluble, its precipitation makes it necessary to conduct a second separation of the precipitated products. But often this can be solved by simply heating. To achieve high conversions at elevated temperatures is is desirable to maintain the system under pressure of carbon dioxide. Rates are very high at elevated temperatures, even with chunks of some of the metal carbonates, especially dolomite.

While water is the preferred media of the process, it does proceed almost equally well in mixtures of water with methanol and acetone. In fact the process can be conducted in methanol, but more sluggishly. In whatever media, by adding the metal carbonate and alkali oxalate and optionally carbon dioxide continuously, the process can be made to be continuous.

Ideally the process conducted using water or methanol as the media is conducted at roughly 50° C at atmospheric pressure or using carbon dioxide bubbled into the liquid at only that pressure required. However, for forms of carbonates which do not react rapidly, it may be desireable or necessary to conduct the process at temperatures well above 100° C necessitating pressures up to 20 atmospheres. This is especially true using natural minerals which contain silicates and sulfides in addition to carbonates.

A number of the oxalates prepared by the process are simply means for obtaining other compounds. Thus limestone is very cheap and leads to calcium oxalate and sodium carbonates when reacted with sodium oxalate in water. But thermal decomposition of calcium oxalate yields calcium carbonate and represents an expensive route to limestone. As noted earlier, calcium oxalate is commercially treated with dilute sulfuric acid to produce oxalic acid. In copending application 551,151 filed Mar. 4, 1975, I disclose a process for the production of ammonium oxalate from calcium oxalate and ammonium carbonate. Similarly, British Pat. No. 517,455 describes the conversion of calcium oxalate to copper ammonium complex solutions and precipitated calcium carbonate through the use of a copper salt and ammonium carbonate.

French Pat. No. 893,255 discloses the earlier noted separation of mixed magnesium-calcium oxalates obtained using dolomite. Magnesium oxalate can be thermally decomposed to magnesium oxide, or can be used as an intermediate to magnesium compounds, for example magnesium sulfate. As noted earlier, a number of oxalates decompose in nitrogen or hydrogen at very low temperatures to metals, including cobalt, copper, iron, nickel, silver and others. Manganese oxalate is useful in preparing ferrites by thermal decomposition with mixtures of other oxalates such as iron and zinc oxalates. But manganous oxalate is an excellent source of divalent manganese for the production of manganese sulfate which is electrolyzed to metallic manganese. Thus the process of the present invention not only provides a means for refining carbonates but also yields valuable intermediates.

The value of the alkali metal carbonates is well known. As noted herein, ammonium carbonate can be a valuable intermediate in the reverse process. Usually the best means for recovering the carbonates from the solutions obtained in the present invention is simply to cool with further carbonation, precipitating the bicarbonate which normally has a lower solubility than the carbonate, lithium carbonate the exception. But isolation by evaporation is a reasonable way to recover the potassium carbonates since both the bicarbonate and carbonate are fairly soluble.

According to the provision of the patent statutes. I have explained the principle of my invention and have illustrated and described what I now consider to represent its best embodiment. However, I desire to have it understood that within the scope of the appended claims, the invention may be practiced otherwise than as specifically illustrated and described.

I claim:

1. A process for the production of alkali metal carbonates and metal oxalates wherein the metal is other than an alkali metal, which comprises reacting an alkali metal oxalate with a metal carbonate in a liquid media selected from water, methanol, water-methanol mixtures and water acetone mixtures, at a temperature in the range of −30° C to 300° C under conditions sufficient to maintain said liquid media in the liquid state to produce alkali metal carbonate and metal oxalate.

2. A method according to claim 1 wherein the pH of the reaction is maintained below about 11 by the addition of carbon dioxide.

3. The process of claim 1 where said metal carbonate is calcium carbonate and said alkali metal oxalate is sodium oxalate.

* * * * *